(12) United States Patent
Pretz et al.

(10) Patent No.: US 10,272,407 B2
(45) Date of Patent: Apr. 30, 2019

(54) APPARATUS USED IN A FLUIDIZED REACTION PROCESS

(71) Applicant: Dow Global Technologies LLC, Midland, MI (US)

(72) Inventors: Matthew T. Pretz, Freeport, TX (US); Don F. Shaw, Rockaway, NJ (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 15/533,508

(22) PCT Filed: Dec. 14, 2015

(86) PCT No.: PCT/US2015/065471
§ 371 (c)(1),
(2) Date: Jun. 6, 2017

(87) PCT Pub. No.: WO2016/100169
PCT Pub. Date: Jun. 23, 2016

(65) Prior Publication Data
US 2017/0361295 A1  Dec. 21, 2017

Related U.S. Application Data

(60) Provisional application No. 62/092,947, filed on Dec. 17, 2014.

(51) Int. Cl.
*B01J 19/18* (2006.01)
*B01J 8/26* (2006.01)
(Continued)

(52) U.S. Cl.
CPC .............. *B01J 8/1854* (2013.01); *B01J 8/005* (2013.01); *B01J 8/0055* (2013.01); *B01J 8/1872* (2013.01);
(Continued)

(58) Field of Classification Search
CPC .................. B01J 8/1854; B01J 8/1872; B01J 2208/00796
See application file for complete search history.

(56) References Cited

U.S. PATENT DOCUMENTS

| 2,672,407 A | 3/1954 | Leffer |
| 2,727,810 A | 12/1955 | Leffer |

(Continued)

FOREIGN PATENT DOCUMENTS

| WO | 2013009820 A1 | 1/2013 |
| WO | 2016100169 A1 | 6/2016 |

OTHER PUBLICATIONS

PCT/US2015/065471 International Search Report and Written Opinion dated May 6, 2016.

(Continued)

*Primary Examiner* — Lessanework Seifu
(74) *Attorney, Agent, or Firm* — Dinsmore & Shohl LLP (57) ABSTRACT

An apparatus used in a fluidized reaction process comprising a vessel; a riser housed within the vessel; and a plurality of angled guide supports, wherein each guide support comprises an tubular section having a first end and a second end; a first hinge wherein a first end of the first hinge is connected to the first end of the tubular section, a second hinge wherein a first end of the second hinge is connected to the second end of the tubular section, wherein a second end of the first hinge is connected to an inside surface of the vessel and a second end of the second hinge is connected to the riser guide is provided.

10 Claims, 7 Drawing Sheets

(51) Int. Cl.
*B01J 8/18* (2006.01)
*B01J 8/00* (2006.01)
*C07C 5/333* (2006.01)

(52) U.S. Cl.
CPC ............... *B01J 8/26* (2013.01); *C07C 5/333* (2013.01); *B01J 2208/00796* (2013.01)

(56) References Cited

U.S. PATENT DOCUMENTS

| | | |
|---|---|---|
| 2,828,281 A | 3/1958 | Groote et al. |
| 2,943,922 A | 7/1960 | Daniels |
| 3,948,609 A | 4/1976 | Guseinov et al. |
| 7,902,101 B2 | 3/2011 | Hedrick et al. |

OTHER PUBLICATIONS

PCT /US2015/065471 International Preliminary Report on Patentability dated Jun. 29, 2017.
Examination Report pertaining to GCC patent Application 2015-30535, dated Apr. 11, 2018.
Second Examination Report pertaining to GCC patent application No. 2015-30535, dated Aug. 8, 2018.

APPARATUS USED IN A FLUIDIZED REACTION PROCESS

FIELD OF INVENTION

The disclosure relates to an apparatus used in a fluidized reaction process.

BACKGROUND OF THE INVENTION

In many fluidized reaction processes such as Fluidized Catalytic Cracking (FCC), Methanol to Olefins, Catalytic Dehydrogenation, and the like, there are risers in each of the catalyst regenerator vessels and the fluidized catalyst-hydrocarbon product separation vessels commonly referred to as reactors in FCC. In the case of the catalyst regenerator vessel, the riser extends vertically into the regenerator dilute phase (freeboard) to allow sufficient volume for catalyst to accumulate below the device in the annular space. In the case of the fluidized catalyst hydrocarbon product separation vessel (commonly referred to as the reactor in FCC), the riser performs the reaction and transports catalyst to the cyclonic separation device(s). Consequently because of the long length and high temperature, the riser which is supported at the bottom of the vessel at a fixed location must be guided for lateral support while accommodating expansion and contraction. The manner of guiding the riser must be flexible to account for the high axial thermal expansion of the riser relative to the vessel shell.

SUMMARY OF THE INVENTION

The disclosure provides a novel riser guide and support apparatus for use in fluidized reaction processes. The apparatus provides lateral guiding for the riser, directly or indirectly, within the vessel. Furthermore, the apparatus guides the riser during significant thermal expansions, both horizontal and vertical, during operation of the fluidized reaction process.

DETAILED DESCRIPTION OF THE INVENTION

In one embodiment, the disclosure provides an apparatus used in a fluidized reaction process comprising: a vessel; a riser housed within the vessel; and a plurality of angled guide supports, wherein each guide support comprises an tubular section having a first end and a second end; a first hinge wherein a first end of the first hinge is connected to the first end of the tubular section, a second hinge wherein a first end of the second hinge is connected to the second end of the tubular section, wherein a second end of the first hinge is connected to an inside surface of the vessel and a second end of the second hinge is connected to the riser guide.

The hinge, as used herein, is a component which bends permitting rotation of the tubular section. For example, the hinge may be a flexible metal sheet or plate or a flexible metal rod or pin.

As used herein, the term "connected" means direct or indirect attachment or insertion. For example, "the second end of the first hinge is connected to an inside surface of the vessel" means that the second end may be attached directly onto the inside surface or, alternatively, the second end may be attached to a plate which in turn is attached directly onto the inside surface of the vessel.

The riser guide, as used herein, means any circumferentially continuous structure around the outside of the riser. For example, the riser guide may be continuous metal ring encircling the riser. Alternatively, the riser guide could be a plurality of plates linked by a continuous circular band encircling the riser.

As used herein, the tubular section is a solid or hollow member, such as a pipe, which is more rigid than the hinges and which may have any cross-sectional shape, including but not limited to square, rectangular, circular, cross-shaped, T-shaped and I-shaped.

Figure 1:
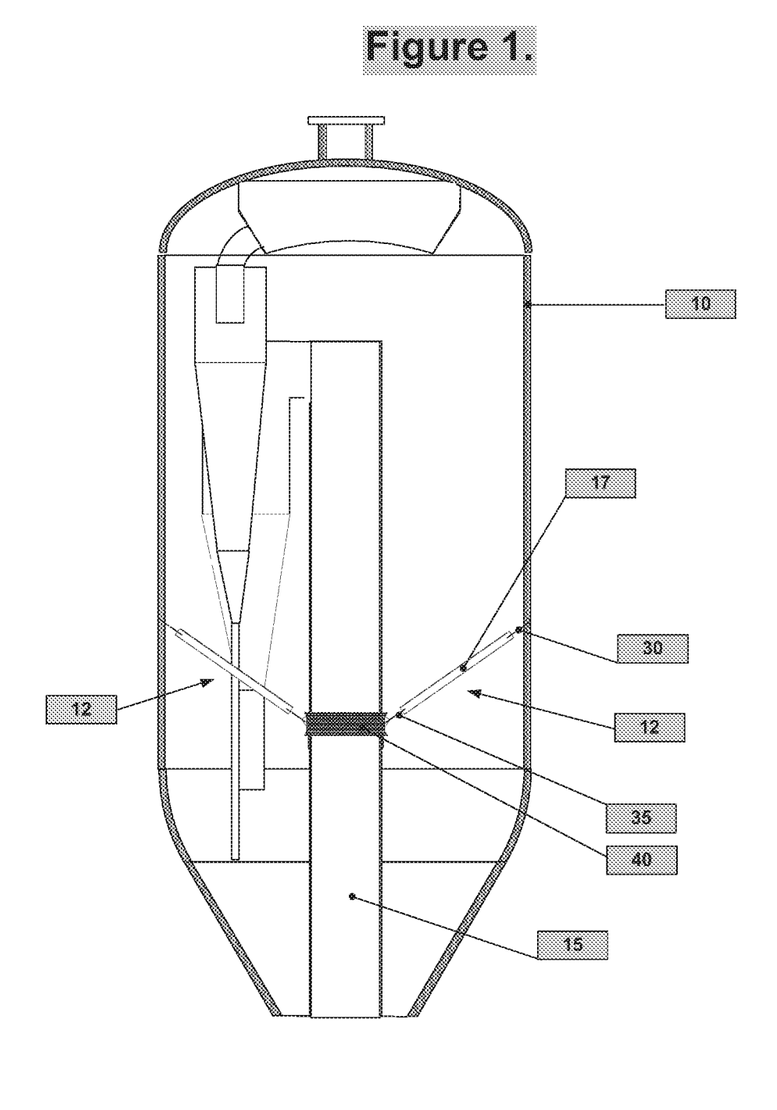
FIG. 1 is a schematic illustrating a first embodiment of the inventive apparatus as used in a fluidized catalyst hydrocarbon separation vessel.
Figure 2:
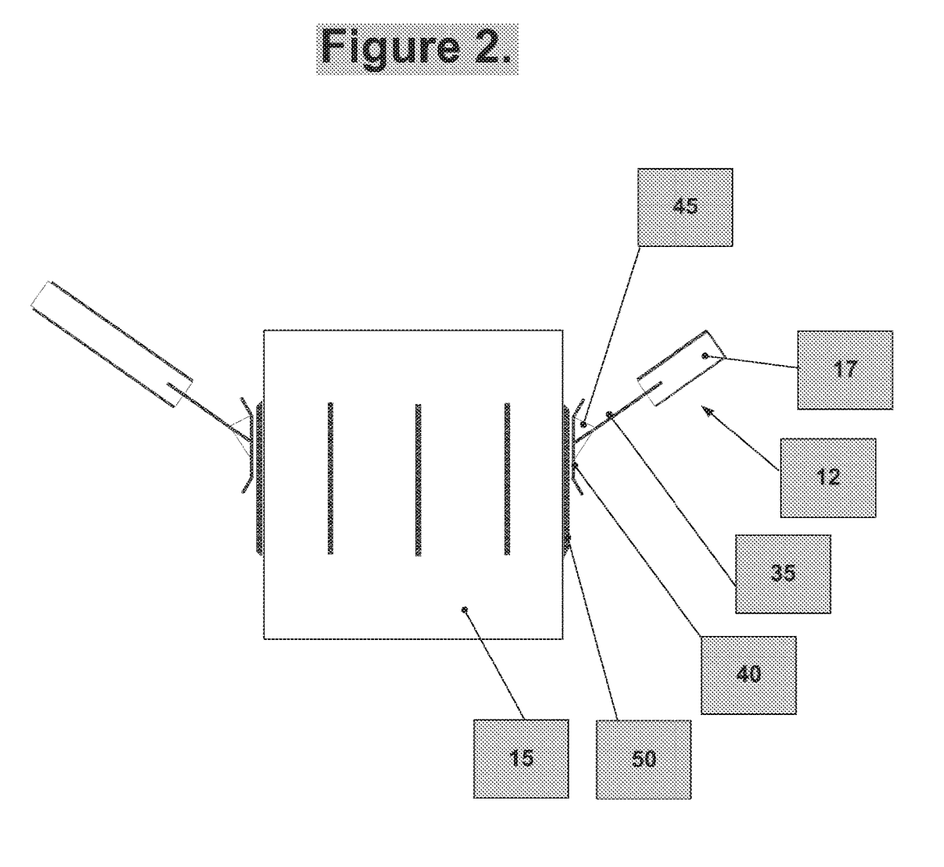
FIG. 2 is a schematic illustrating an expanded view of the attachment of the support 12 to the riser guide 40 as shown in less detail in FIG. 1.

Referring to FIG. 1, a first embodiment of the inventive apparatus is shown wherein the apparatus is used in connection with a fluidized catalyst hydrocarbon separation vessel 10 housing a riser 15 which is encircled by a riser guide 40. As can be seen in FIG. 1, the apparatus includes a plurality of angled guide supports 12. Each guide support 12 comprises a tubular section 17 with a first hinge 30 connected to a first end of the tubular section 17 and a second hinge 35 connected to a second end of the tubular section 17. FIG. 2 shows an expanded cross sectional view of the attachment of the second hinge 35 of the guide support 12 to the riser guide 40. The attachment between the second hinge 35 and the riser guide 40. Gusset 45 provides reinforcement to the joint between the second hinge 35 and the riser guide 40 against, for example, forces induced by lateral vibration of the riser imparted during thermal expansion and contraction. As can be seen in FIG. 2, each gusset 45 is a triangular metal plate welded to the riser guide 40 and to opposing sides of the second hinge 35. As shown in the embodiment in FIG. 1, the riser guide 40 slidably guides the riser by contacting the vertical riser ribs 50 which are located and welded circumferentially around the riser. Alternatively, the riser guide 40 slidably guides the riser 15 in the absence any riser ribs 50.

Figure 3:
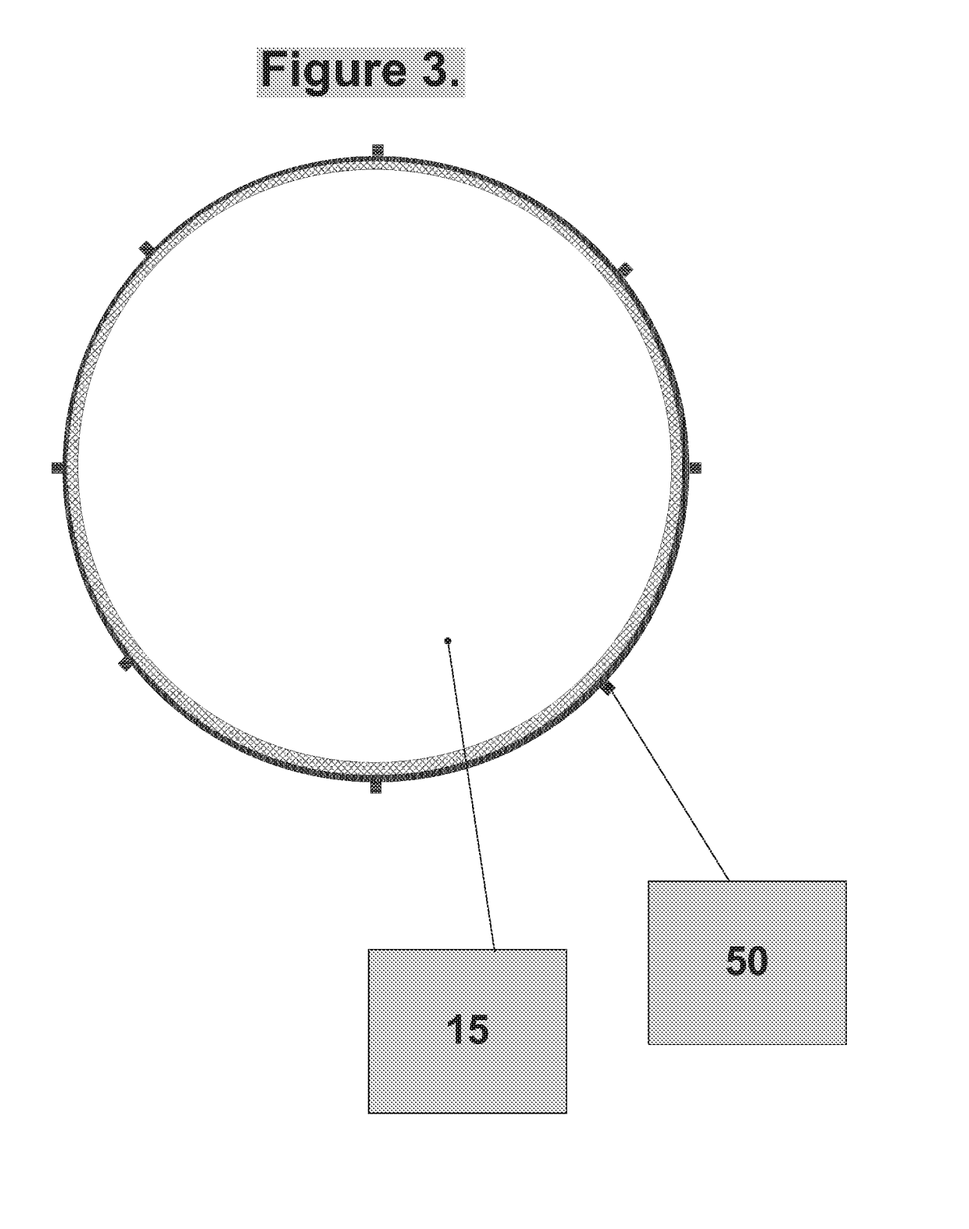
FIG. 3 is a cross sectional view of the riser 15 illustrating a plurality of riser ribs 50.

FIG. 3 is a cross sectional view of the riser 15 illustrating a plurality of riser ribs 50. Riser ribs 50 moderate the effects of mechanical wear and friction with the riser guide on the outside surface of the riser 15. The riser ribs 50 may allow controlled sliding clearance between two concentric parts, the riser and the riser guide, which may not be perfectly concentric or round due to fabrication conditions. The ribs 50 may also control the spacing between the riser 15 and riser guide 40.

Figure 4A:
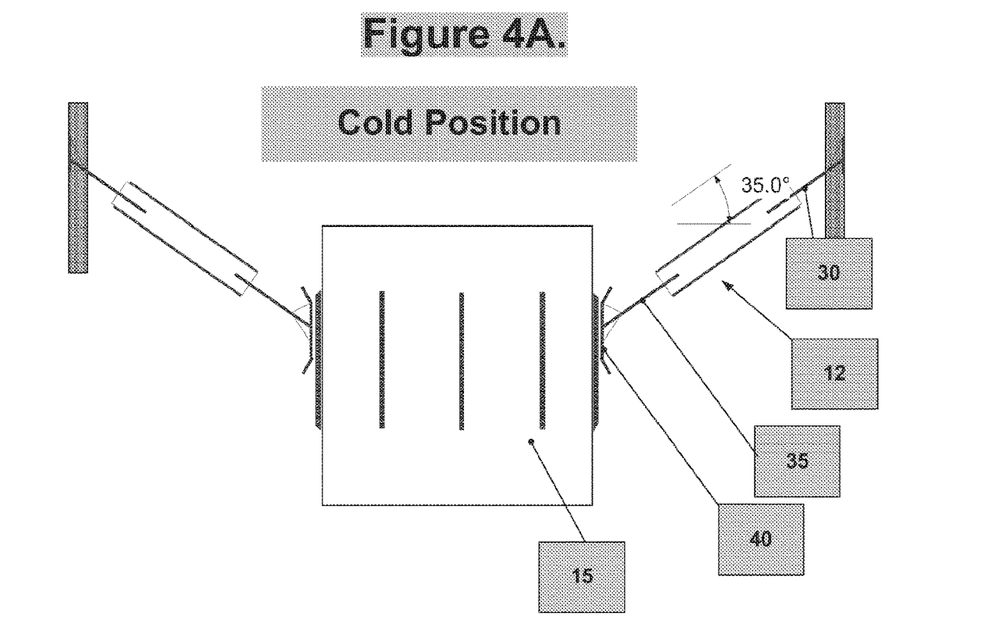
FIG. 4A is a schematic illustrating the position and configuration of a riser support 15 at ambient temperature prior to thermal expansion.
Figure 4B:
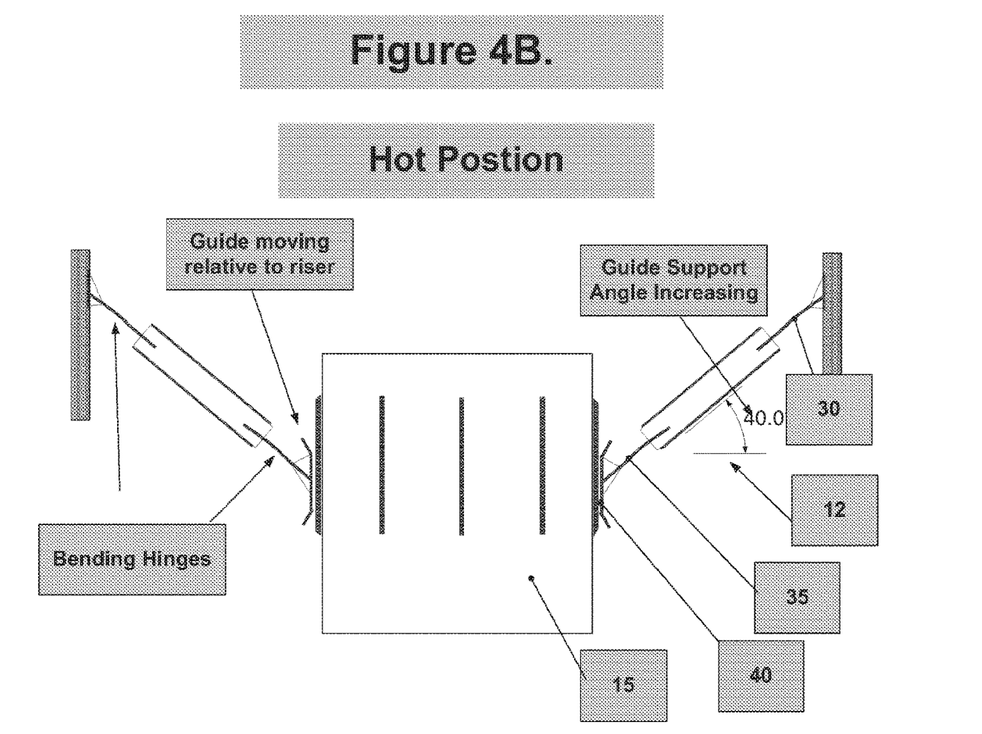
FIG. 4B is a schematic illustrating the position and configuration of a riser support 15 at elevated temperature during thermal expansion.

FIG. 4A illustrates the position and configuration of the riser supports 12 connected to a riser guide 40 at ambient temperatures before any thermal expansion. FIG. 4B illustrates the position and configuration of the riser supports 12 connected to a riser guide 40 at elevated temperatures during thermal expansion. As can be seen in comparing FIGS. 4A and 4B, it can be seen that on expansion of the riser with elevated temperature, the riser expands upwardly so that the riser guide 40 encircles a lower portion of the riser 15. Furthermore, the hinges 30 and 35 bend and the angle of the supports off of horizontal increases.

Figure 5:
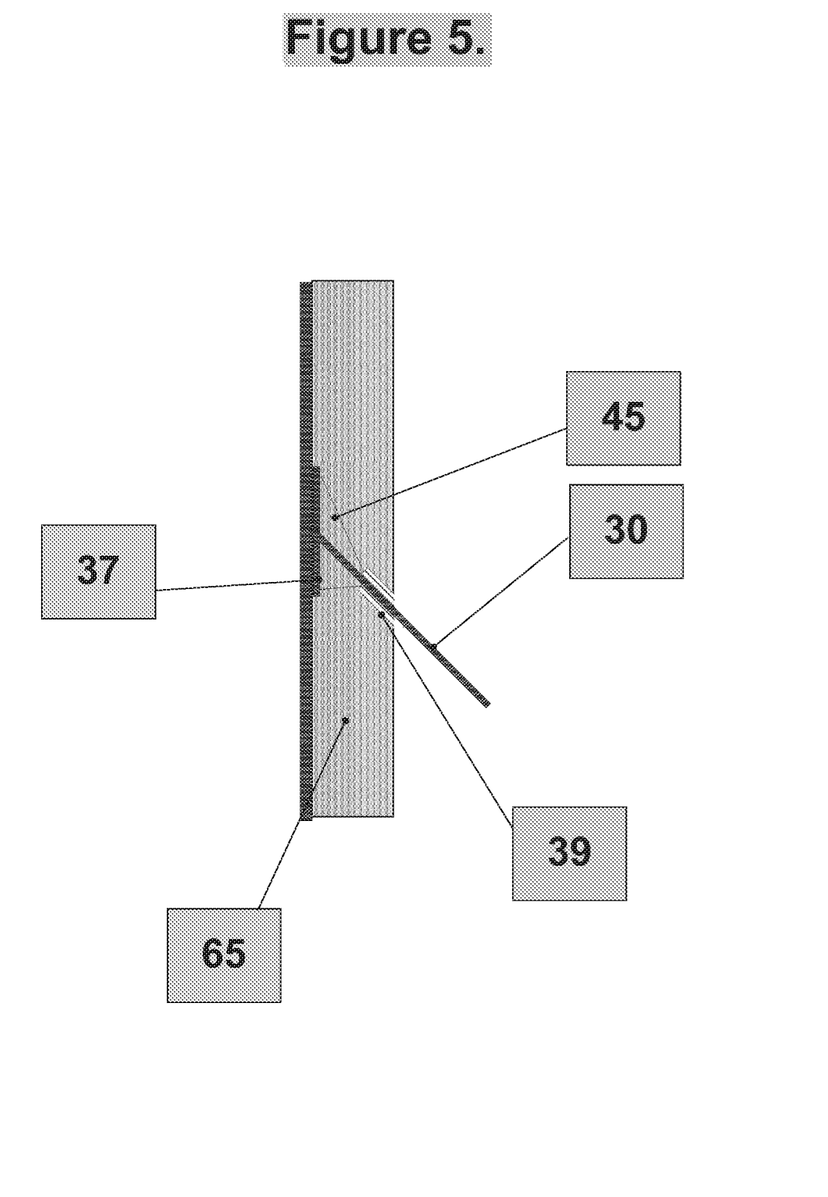
FIG. 5 is an expanded view of the gusset attachment to an inside surface of the vessel 10 as shown in less detail in FIG. 1.

FIG. 5 is a detailed illustration of the gusset attachment to an inside surface of the vessel 10. As shown in FIG. 5, the inside surface of the vessel 10 may be lined with an insulating refractory material 65 to enable the vessel, even if produced from a metal such as carbon steel, to be used at high temperature. Each first hinge 30 passes through the refractory material 65 for attachment to a plate 37 that is welded to the inside surface of the vessel 10. Gusset 45 reinforces the joint between plate 37 and hinge 30. Plate 37 may be used, for example, to provide a locus for a bi-metallic weld in those instances in which the vessel 10 and the hinge 30 are made from different metals. Element 39 is ceramic fiber board placed between the refractory material 65 and the hinge 30 to protect the refractory material 65 during bending and/or deflection of the hinge 30.

Figure 6:
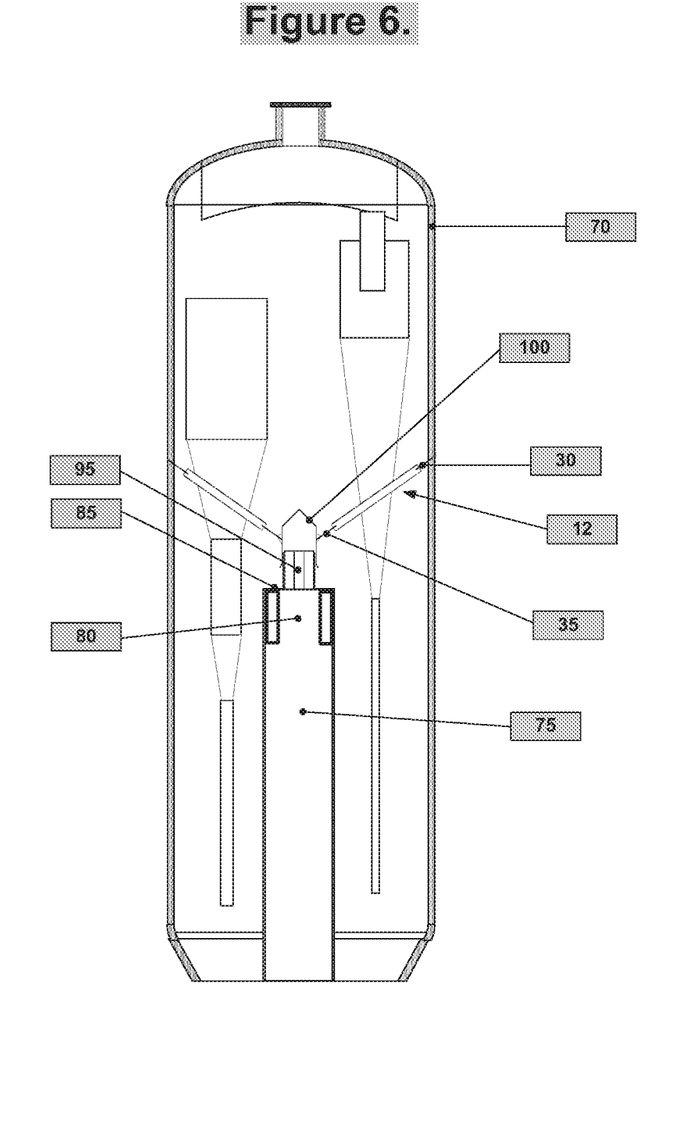
FIG. 6 is a schematic illustrating a second embodiment of the inventive apparatus as used in a catalyst regenerator vessel.

FIG. 6 illustrates another embodiment of the inventive apparatus as used in a catalyst regenerator vessel 70. As shown in FIG. 6, the catalyst regenerator vessel 70 houses a riser 75 in which the catalyst is subjected to extended oxygen treatment. Such extended oxygen treatment is disclosed in commonly owned pending PCT application WO2013/009820, the disclosure of which is incorporated herein by reference. The extended oxygen treatment utilizes a taller riser than is typically seen in such catalyst regenerator vessels. Consequently, support from below the riser 75 may, in some instances, not be sufficient to fully control lateral vibration and stabilize the riser 75 during thermal expansion and contraction during operation. As can be further seen in FIG. 6, the riser 75 terminates in a riser terminator 80. As shown in FIG. 6, the riser terminator 80 has a horizontal top surface 85. It will be readily understood that any shape or configuration of the riser terminator 80 may be used, including different configurations of the top surface 85. As further illustrated, above the horizontal top surface 85 is a riser cap 95. The riser cap 95 may be integral with the riser terminator 80 or may be a separate component which is attached to the top surface 85. An outer shape of the riser cap 95 is configured to fit within a riser guide 100. The riser guide 100 is connected to the inner surface of the catalyst regenerator vessel 70 by way of a plurality of guide supports 12. Each guide support 12 is configured in the same manner as described in FIG. 1. Furthermore, the attachment of each hinge plate, 30 and 35, to the vessel wall or riser guide respectively, is reinforced by a gusset 45. While shown as a flat hinge plate in FIG. 1, hinges 30 and 35 could alternatively be contoured, bent or humped hinge plates. The insertion of the riser cap 95 into the riser guide 100 minimizes the radial movement of the riser 75 during thermal expansion and contraction which may occur in operation of the catalyst regenerator.

The material of construction of the components discussed herein, e.g., tubular section, hinge plates, riser, gussets, is preferably selected for suitability of use with the temperature and pressure of the target process. For cases of catalytic dehydrogenation which operate at high temperatures, a material such as 304H stainless steel may be used.

Figure 7:
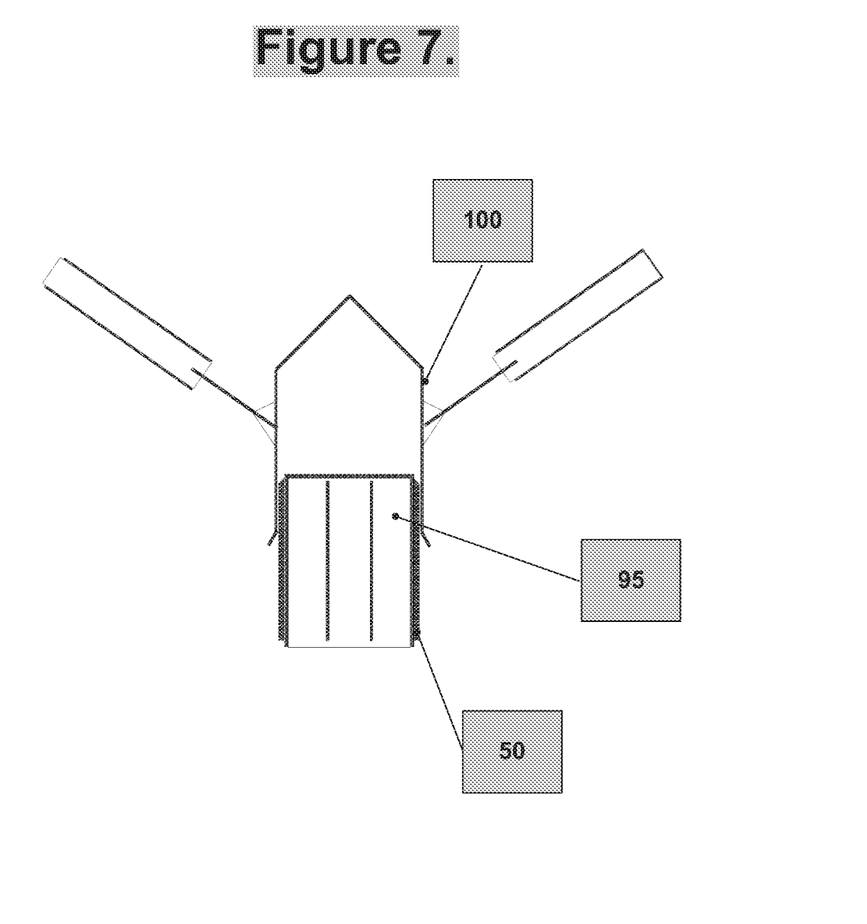
FIG. 7 is an expanded view of the connection of the guide supports to the riser guide shown in less detail in FIG. 6.

FIG. 7 illustrates an expanded view of the slidable connection between the riser cap 95 and the riser guide 100. As can be seen in FIG. 7, an outer surface of the riser cap 95 may include a plurality of ribs 50 so as to minimize mechanical wear of the riser guide 100 and the riser cap 95 during thermal expansion and contraction. Such ribs 50 may extend vertically over only a portion or portions of the riser cap 95 or alternatively, over the entire height of the riser cap 95. In other embodiments such ribs 50 may extend vertically over portions of the riser 75 or alternatively, over the entire height of the riser. In an alternative embodiment, no ribs 50 are used on the outside of the riser cap 95.

It will be further understood that the vessel 70 may be lined with insulating refractory materials as shown in FIG. 5. Alternatively, the vessel may be unlined.

As can be seen in each of FIGS. 1 and 6, the angled supports 12 are attached in a manner provide an angle off of horizontal between the vessel, 10 or 70, and the riser, 15 or 75, respectively. In a specific embodiment, each guide support is at an angle from 5 degrees to 85 degrees off of horizontal. All individual values and subranges from 5 to 85 degrees are included and disclosed herein. For example, the angled supports 12 may be at an angle from 5 to 85 degrees off of horizontal, or in the alternative, from 15 to 60 degrees off of horizontal, or in the alternative, from 20 to 40 degrees off of horizontal. Such angle of attachment is provided to encourage bending in the hinge plates 30 and 35 and sliding of riser guide 40 during vertical and horizontal thermal contraction and expansion. The length of the hinge plates, 30 and 35 and the tubular sections 17 and the angle formed by attachment of the supports 12 will vary based on a number of variables, such as the size of the vessels 10 and 70 and risers 15 and 75, as may be readily determined by a skilled artisan.

In a particular embodiment, the fluidized reaction process is a catalytic propane dehydrogenation process.

The present invention may be embodied in other forms without departing from the spirit and the essential attributes thereof, and, accordingly, reference should be made to the appended claims, rather than to the foregoing specification, as indicating the scope of the invention.

We claim:

1. An apparatus used in a fluidized reaction process comprising:
   a vessel;
   a riser housed within the vessel; and
   a plurality of angled guide supports, wherein each guide support comprises a tubular section having a first end and a second end; a first hinge wherein a first end of the first hinge is connected to the first end of the tubular section, a second hinge wherein a first end of the second hinge is connected to the second end of the tubular section, wherein a second end of the first hinge is connected to an inside surface of the vessel and a second end of the second hinge is connected to a riser guide comprising a circumferentially continuous structure around the outside of the riser.

2. The apparatus of claim 1, further comprising a gusset reinforcing the connection between the second end of the first hinge to the inside surface of the vessel.

3. The apparatus of claim 1, further comprising a gusset reinforcing the connection between the second end of the second hinge and the riser guide.

4. The apparatus of claim 1, wherein the vessel is a catalyst regenerator vessel.

5. The apparatus of claim 4, wherein the riser is an extended catalyst transport riser located in a catalyst reactivation vessel, the riser comprising a riser terminator and a riser cap, wherein the riser terminator has an upper surface, wherein the riser cap is above the upper surface, and wherein the riser cap is slidably inserted into the riser guide such that the riser cap is encircled by the riser guide.

6. The apparatus of claim 1, wherein the vessel is a fluidized catalyst-hydrocarbon product separation vessel.

7. The apparatus of claim 6, wherein the riser is a reactor and catalyst transport pipe located in a catalyst separation zone having an optional plurality of ribs attached to an outer surface of the riser, wherein the riser guide encircles the riser.

8. The apparatus of claim 1, wherein the riser guide is a continuous cylinder.

9. The apparatus of claim 1, wherein the riser guide is connected to the vessel only by the plurality of angled guide supports.

10. The apparatus of claim 1, wherein the riser guide slideably guides the riser as it expands upwards at elevated temperatures.

* * * * *